United States Patent [19]

Olson

[11] Patent Number: 5,458,619
[45] Date of Patent: Oct. 17, 1995

[54] APPARATUS AND METHOD FOR TREATING A TACHYARRHYTHMIA

[75] Inventor: Walter H. Olson, North Oaks, Minn.

[73] Assignee: Medtronci, Inc., Minneapolis, Minn.

[21] Appl. No.: 159,351

[22] Filed: Nov. 29, 1993

[51] Int. Cl.⁶ .................................................. A61N 1/39
[52] U.S. Cl. .................................................. 607/4
[58] Field of Search .................................. 607/4

[56] References Cited

U.S. PATENT DOCUMENTS 5,048,521 9/1991 Pless et al. .................................. 607/4

Primary Examiner—William E. Kamm
Attorney, Agent, or Firm—Reed A. Duthler; Harold R. Patton

[57] ABSTRACT

An antitachyarrhythmia device employing a tachycardia termination methodology in which antitachycardia pacing and cardioversion pulse therapies are combined. After detection of an arrhythmia which would normally result in delivery of a cardioversion or defibrillation pulse, the device begins to charge high voltage output capacitors. During the charging period, the device deliveries an antitachycardia pacing pulse regimen, in an attempt to terminate the arrhythmia prior to delivery of the cardioversion or defibrillation pulse. Following delivery of the antitachycardia pacing pulse regimen, the device evaluates the heart rhythm to determine whether the tachyarrhythmia has terminated. If so, delivery of a high voltage cardioversion or defibrillation pulse is aborted. If the tachyarrhythmia has not terminated, the high voltage pulse is delivered.

18 Claims, 11 Drawing Sheets

APPARATUS AND METHOD FOR TREATING A TACHYARRHYTHMIA

BACKGROUND OF THE INVENTION

This invention relates generally to implantable medical stimulators, and more particularly to implantable pacemaker/cardioverter/defibrillators.

Implantable pacemaker/cardioverter/defibrillators, of the types presently in clinical evaluation include the capability to detect the occurrence of tachycardias and fibrillation. In response to detection of tachycardias, anti-tachycardia pacing therapy or high voltage cardioversion pulses may be delivered. In response to detection of fibrillation, high voltage defibrillation pulses are typically the only therapy delivered. Traditionally, anti-tachycardia pacing and cardioversion have been used as alternative therapies, with cardioversion typically used when anti-tachycardia pacing fails to terminate a detected tachycardia, when a detected tachycardia accelerates or when the rate of the detected tachycardia meets a predetermined fast tachycardia rate threshold. U.S. Pat. No. 4,830,006, issued to Haluska et al., U.S. Pat. No. 4,971,058, issued to Pless et al., U.S. Pat. No. 5,161,527, issued to Nappholz et al. and U.S. Pat. No. 5,002,052, issued to Haluska disclose devices which function in these fashions.

High voltage cardioversion and defibrillation pulses are typically delivered using high voltage output capacitors not used for delivery of pacing pulses. These capacitors are typically charged in response to detection of a tachycardia or fibrillation, rather than maintained in a charged condition. As a result, a substantial amount of time may pass between detection of the arrhythmia and delivery of the high voltage pulse.

High voltage pulses are extremely painful in many cases and impose a substantial current drain on the battery of the implanted device. Therefore, avoiding inappropriate delivery of such pulses is recognized to be desirable. It has been recognized that the arrhythmia may change during charging. As a result, sensing the rhythm during charging has been proposed. For example in U.S. Pat. No. 4,949,719, issued to Pless et al, and U.S. Pat. No. 5,191,884, issued to Gilli et al, the implanted device checks during charging to determine whether the arrhythmia has spontaneously terminated and aborts the charging of the output capacitors if the rhythm has returned to normal. While this feature in some cases accomplishes the desired result of avoiding unnecessary shocks, further reductions in the frequency of delivery of such shocks are still desirable.

SUMMARY OF THE INVENTION

The present invention is directed toward reducing the number of high voltage cardioversion and defibrillation shocks delivered by an implantable pacemaker/cardioverter/defibrillator. Rather than simply attempting to determine whether the detected tachyarrhythmia has spontaneously terminated during or after charging of the high voltage output capacitors, a device according to the present invention delivers an anti-tachycardia pacing therapy during charging of the high voltage capacitors.

The pacing therapy may be selected such that its duration will allow complete delivery prior to expected completion of high voltage capacitor charging, to avoid undue delay in delivery of the scheduled high voltage pulse. However, a pacing therapy which lasts longer than expected capacitor charging time may also be selected, especially in those instances where the voltage of the scheduled cardioversion or defibrillation pulse is relatively low, so that only a relatively short charge time is available for delivery of the anti-tachycardia pacing therapy.

Following charging of the output capacitors, the device employs a confirmation and synchronization function which determines whether the delivered pacing therapy was effective in terminating the tachyarrhythmia and, if not, provides synchronized defibrillation or cardioversion, as is appropriate. If the device is capable of sensing during charging, it may also detect termination following delivery of the pacing therapy, prior to completion of capacitor charging, and abort delivery of the scheduled cardioversion or defibrillation pulse.

The anti-tachycardia pacing therapy chosen for delivery during the charging of the output capacitors may be predetermined, or may be selected by the device based on the anticipated time required to charge the output capacitors to the voltage of the output pulse, and/or depending upon what anti-tachycardia pacing therapies, if any, have previously been delivered and have been determined to be successful in terminating tachycardia.

DETAILED DESCRIPTION OF THE PREFERRED EMBODIMENTS

Figure 1:
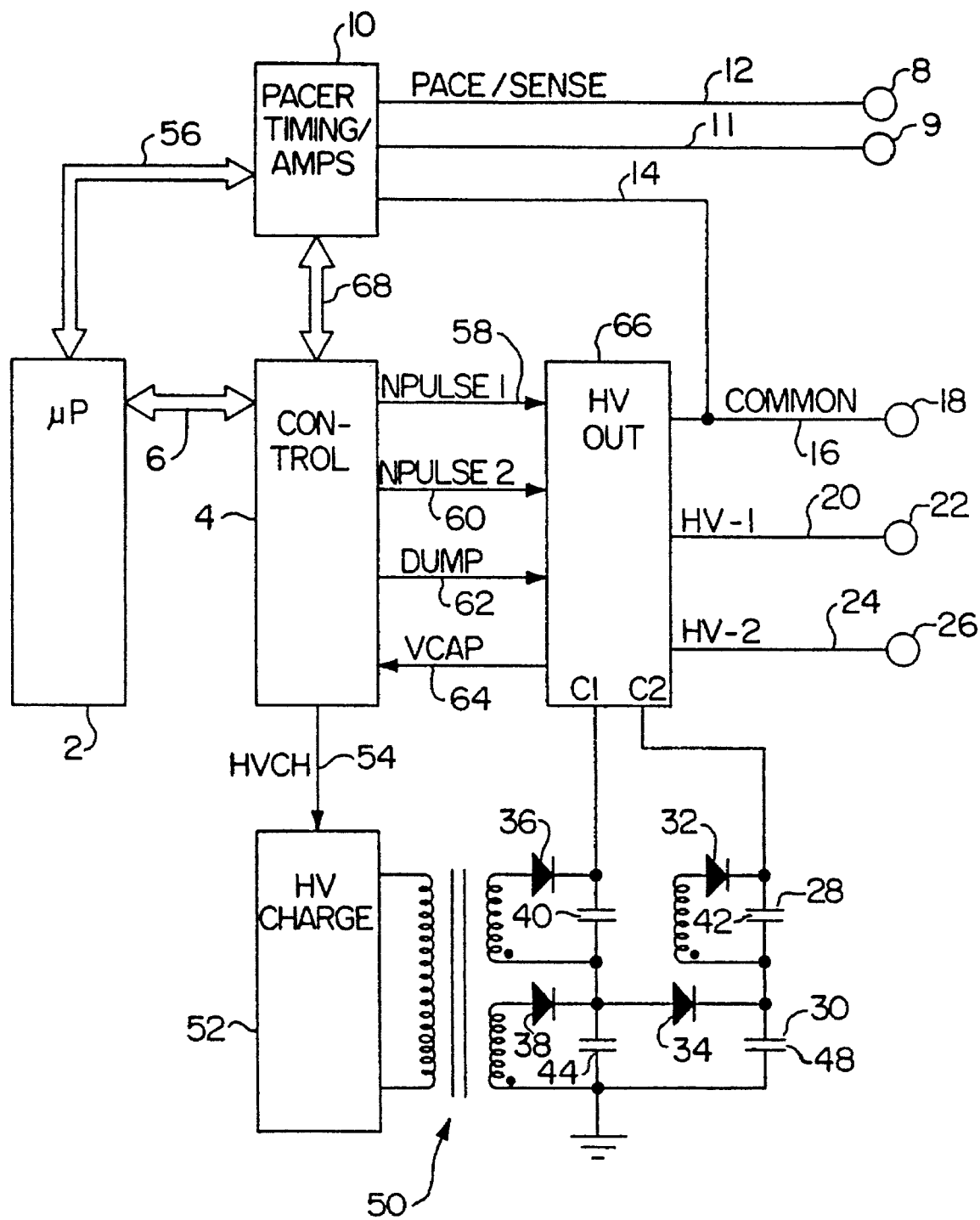
FIG. 1 is a block, functional diagram of an implantable pacemaker/cardioverter/defibrillator adapted to perform the synchronization methodology of the present invention.

FIG. 1 is a block, functional diagram illustrating an implantable pacemaker/cardioverter/defibrillator embodying the present invention. The device includes a microprocessor 2, which holds a stored program controlling the operation of the device. Microprocessor 2 includes a read-only memory, containing the firmware controlling the basic operation of the device, a random access memory, for storing measured parameters and for storing instructions related to variable operating procedures within the device, and also includes an arithmetic logic unit enabling the microprocessor to calculate the various time periods required by the device.

The second major block of the device is the control block 4, which serves to control operation of the high voltage output stage 66, which controls delivery of high energy cardioversion and defibrillation pulses to the electrodes 18, 22 and 26. Control signals and information pass between microprocessor 2 and control block 4 by means of a bi-directional data/control bus 6. Depending upon the particular pulse regimens programmed, microprocessor 2 enables control block 4 to trigger the delivery of the cardioversion and/or defibrillation pulses of the desired amplitude and pulse configuration. The interrelation of control circuitry 4 with high voltage output circuitry 66 is discussed in more detail in commonly assigned U.S. Pat. No. 5,163,427, issued to Keimel and incorporated herein by reference in its entirety. However, for the sake of the present application, it is believed sufficient to note that in response to a logic signal on signal NPULSE 1 line 58, capacitors 40 and 44 are discharged between electrodes 18 and 22, while in response to a logic signal on NPULSE 2 line 60, capacitors 40, 42, 44 and 48 are discharged through electrodes 18 and 26. The signals on NPULSE-1 line 58 and NPULSE-2 line 60 may be provided sequentially, simultaneously or individually.

Control block 4 also provides a signal on HVCH line 54 initiating the high voltage charging circuitry 52, during which the capacitors 40, 42, 44 and 48 are charged by means of high voltage transformer 50. Proper charging polarity is maintained by diodes 32, 34, 36 and 38. VCAP line 64 from high voltage output circuitry 66 provides a measurement of the voltage stored on the capacitors 40, 42, 44 and 48 to the control circuitry 4, so that it may terminate charging of the capacitors by means of HVCH line 54, when their voltage equals the voltage selected by microprocessor 2. Dump line 62 from control block 4 initiates discharge of capacitors 40, 42, 44 and 48 through an internal resistance, under the circumstances described below. Again, the operation of the high voltage output circuitry in conjunction with the output capacitors 40, 42, 44 and 48 is described in detail in the above-cited Keimel patent. For purposes of the present application, however, it is believed sufficient to note that the signal on VCAP line 64 reflects the voltage stored on capacitors 40 and 44, and that the Dump line 62 initiates discharge of all four capacitors.

The device also includes cardiac pacemaker circuitry 10, which includes circuitry employed to control timing of cardiac pacing, an R-wave sense amplifier for detection of ventricular depolarizations via electrodes 8 and 9 or 18 and an output circuit for delivering cardiac pacing pulses between electrodes 8 and 9 or 18.

The R-wave amplifier employed in pacer circuitry 10 may be an amplifier according to U.S. Pat. No. 5,117,824 issued to Keimel et al., also incorporated herein by reference in its entirety. While this type of amplifier is believed particularly valuable in the context of an implantable pacemaker/cardioverter/defibrillator, other R-wave amplifiers known to the art may also be employed. Signals indicative of the occurrence of sensed R-waves and of cardiac pacing pulses are provided to control circuitry 4, via bi-directional bus 68.

The basic operation of the device is controlled by microprocessor 2, in conjunction with pacer circuitry 10 and control block 4. Pacer circuitry 10 includes a plurality of counters which time intervals associated with the bradycardia pacing. These intervals include a bradycardia pacing escape interval, representing the interval between successive cardiac pacing pulses and between sensed R-waves and the next subsequent cardiac pacing pulses. At the expiration of the bradycardia pacing escape interval, a ventricular pacing pulse is delivered. In response to sensing of an R-wave, the bradycardia escape interval is re-initiated. Pacer circuitry 10 also defines a blanking period, during which R-waves are not sensed by the R-wave amplifier in pacer circuitry 10 and a refractory period, during which R-waves are sensed, but are ineffective to re-initiate timing of the bradycardia pacing escape interval. Signals indicative of the occurrence of sensed R-waves and cardiac pacing pulses are passed to processor 2 as interrupts, awakening the microprocessor and allowing it to perform any necessary calculations. Microprocessor 2 controls the values timed by the timers in pacer circuitry 10 by means of control/data bus 56.

R-waves sensed by pacer block 10 are also employed by microprocessor 2 in performing tachycardia and fibrillation detection. Tachycardia and fibrillation detection algorithms believed appropriate for use in conjunction with the present invention are disclosed in the article "Onset and Stability for Ventricular Tachyarrhythmia Detection in an Implantable Pacer-Cardioverter Defibrillator" by Olson et al., published in Computers in Cardiology, October 1986, pages 167–170 and incorporated herein by reference in its entirety. However, the present invention is also believed workable in conjunction with any of the numerous alternative fibrillation and tachycardia detection algorithms known to the art, including those disclosed in U.S. Pat. No. 4,971,058 issued to Pless et al., U.S. Pat. No. 4,693,253 issued to Adams, U.S. Pat. No. 4,384,585 issued to Zipes, and U.S. Pat. No. 4,830,006 issued to Haluska et al., all of which are incorporated herein by reference in their entirety.

Microprocessor 2 also responds to interrupts indicating the occurrence of sensed R-waves to determine whether previously sensed fibrillation or tachycardias have terminated. In the context of the present invention, it is suggested that termination of tachycardia be verified by the sensing of a sequence of R-R intervals (intervals separating R-waves), each of which exceeds a predetermined tachycardia detection interval. Detection of fibrillation termination may also be accomplished by means of the detection of a predetermined number of R-R intervals, all having durations in excess of a predetermined fibrillation detection interval. However, other termination detection methods are also believed workable in the context of the present invention.

Figure 2:
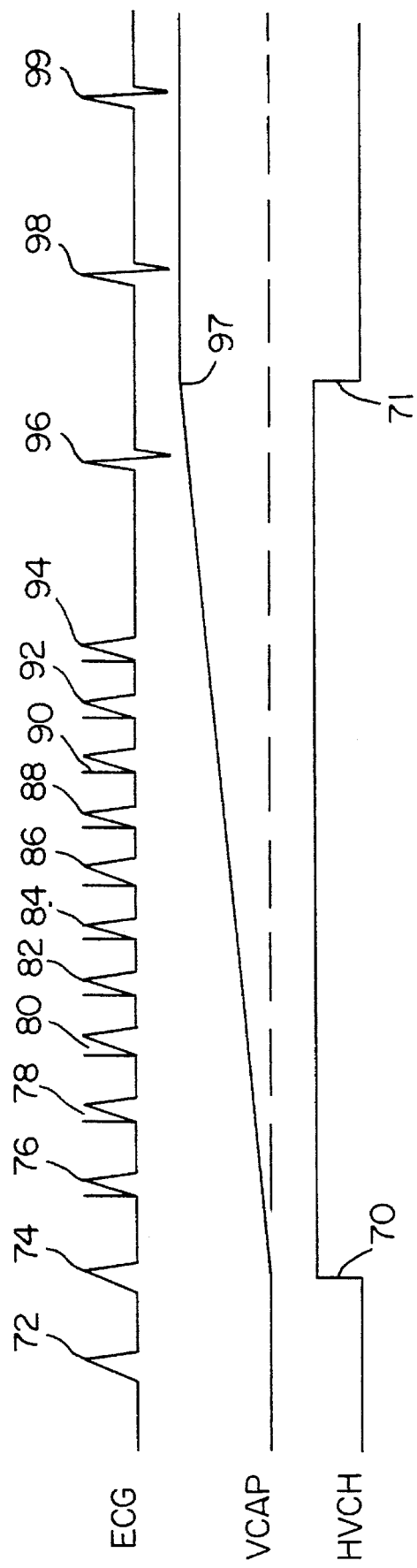
FIG. 2 is a timing diagram illustrating the operation of a device embodying the present invention as it delivers an anti-tachycardia pacing therapy during charging of the high voltage output capacitors.

FIG. 2 is a simulated EKG and timing diagram illustrating the operation of a device according to the present invention in delivering an anti-tachycardia pacing therapy during charging of the high voltage capacitors. The voltage on the output capacitors is indicated by the tracing labelled VCAP, and the logic level of the HVCH line 54 (FIG. 1) is illustrated as well.

In response to detection of a tachyarrhythmia, HVCH line 54 (FIG. 1) is set high at 70, initiating delivery of an anti-tachycardia pacing therapy. As illustrated, the anti-tachycardia pacing therapy delivered is a ten pulse, adaptive ramp pulse sequence, including pacing pulses 76, 78, 80, 82, 84, 86, 88, 90, 92 and 94. The interval separating sensed depolarization 74 from pacing pulse 76 is a percentage of the sensed average time interval between preceding depolarizations prior to detection of the arrhythmia. The interval between pacing pulses is gradually decremented until it reaches a minimum pacing pulse interval, e.g., 250 milliseconds.

As illustrated, following the delivery of the ramp pacing, normal sinus rhythm returns as illustrated by spontaneous depolarizations 96, 98 and 99. As discussed below, following cessation of charging, the apparatus examines the following series of R-waves to determine whether the tachycardia has terminated, or whether the initially detected arrhythmia persists, requiring delivery of a high voltage cardioversion or defibrillation pulse.

For purposes of the present invention, any of the numerous known anti-tachycardia pacing therapies may be employed during the charging period. The two therapies most likely to be employed are single pulse trains of burst or ramp pacing, with the number of pulses in the burst preferably selected so that the entire burst can be delivered prior to expiration of the expected charging time of the high voltage output capacitors. During delivery of the anti-tachycardia pacing therapy, the sense amplifiers may be disabled, in which case the pacing therapy would be delivered synchronized to the final R-wave of the detected arrhythmia, but otherwise asynchronously. If the sense amplifiers are enabled, demand anti-tachycardia pacing may be delivered.

In burst pacing a series of ventricular pacing pulses is delivered at pulse intervals equal to a percentage of the average cycle length of the four R-R intervals preceding detection of the tachyarrhythmia. The physician may program the number of pulses per burst, the percentage of tachycardia cycle length. The burst pulses may be delivered in demand mode or optionally in asynchronous mode. In ramp pacing a series of pacing pulses is also delivered, the first pulse interval being equal to a percentage of the average cycle length of the four R-R intervals preceding detection of the tachyarrhythmia, with the interval between pulses deceasing with each pulse delivered. The physician may program the number of pulses in the ramp, the percentage of tachycardia cycle length for the first interval and the decrement in percentage of cycle length with each successive pulse. The pulses may be delivered in demand mode or in asynchronous mode.

Basic operation of the invention can be understood by reference to the flow charts illustrated in FIGS. 8 through 11. These flow charts are intended to reflect the overall function of the device, rather than any particular software or firmware which must be employed in the device. Because the invention is not dependent upon any particular software or firmware configuration in order to be practiced, the flow charts illustrated focus on the functional aspects of the invention and their interrelation to an implantable pacemaker/cardioverter/defibrillator which includes fibrillation and tachycardia detection function and appropriate hardware for initiation of anti-tachycardia pacing, cardioversion and defibrillation pulses.

Figure 8:
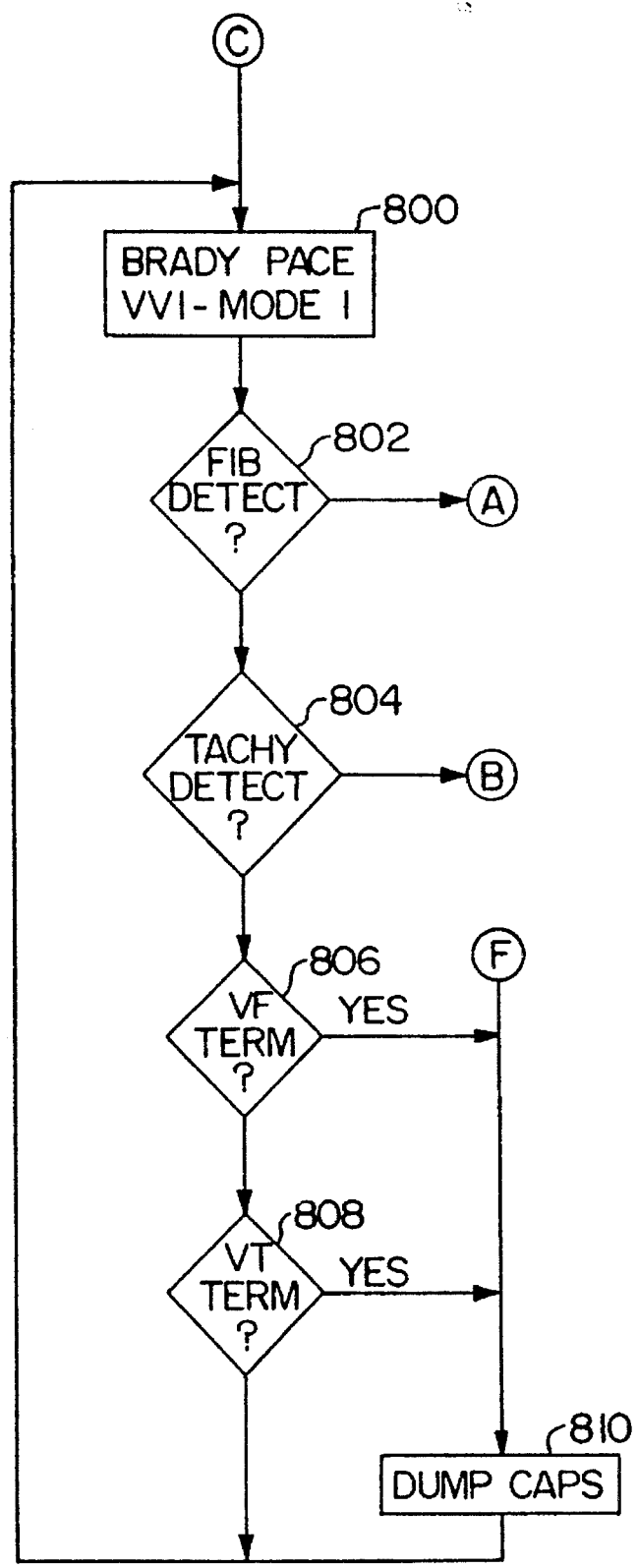
FIGS. 8 through 11 are functional flow charts illustrating the operation of a device embodying the present invention.
Figure 9:
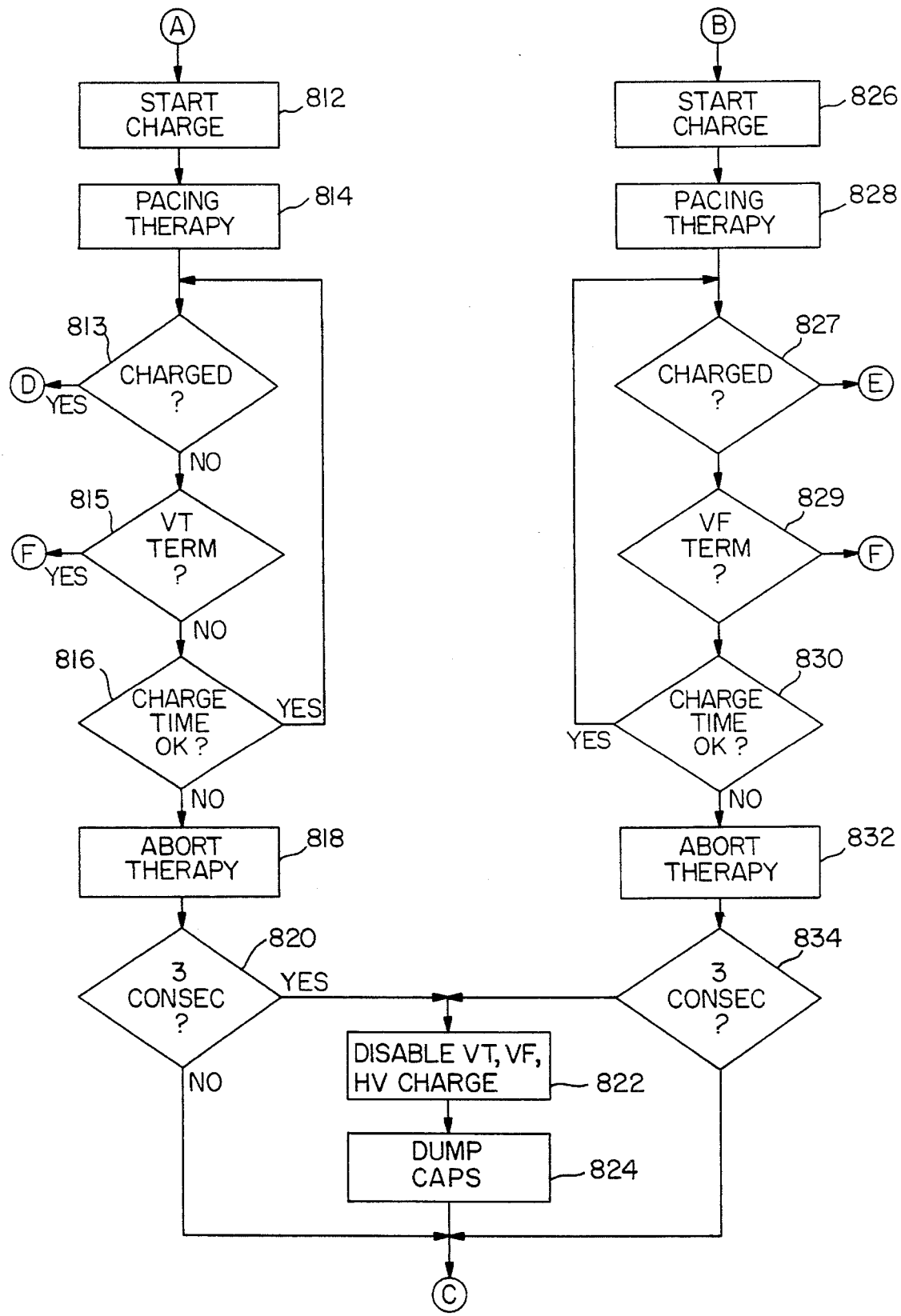

FIG. 8 illustrates the normal operation of the device during bradycardia pacing. Block 800 reflects the fact that the device is executing bradycardia pacing in "Mode 1". For purposes of the present application Mode 1 should be considered to be VVI bradycardia pacing at the programmed parameters. In response to an interrupt indicating occurrence of a pacing pulse or a sensed R-wave, the microprocessor is awakened. Based on the timing of the detected R-wave and/or cardiac pacing pulse, the microprocessor determines whether fibrillation is present at 802. If fibrillation is not present, the microprocessor determines whether tachycardia is present at 804.

Assuming that fibrillation and tachycardia are not found to be present, the microprocessor checks to determine whether fibrillation, if it previously had been detected, has now terminated at 806, and determines whether ventricular tachycardia, if previously detected, has terminated at 808. In the event that termination of fibrillation or tachycardia is detected, the microprocessor triggers control circuitry 4 to cause discharge of the output capacitors 40, 42, 44, and 48 by means of a logic signal on DUMP line 62, and the device continues to function in the programmed bradycardia pacing mode.

In the event that fibrillation or tachycardia is detected, microprocessor 2 may trigger control circuitry 4 to begin charging output capacitors 42, 44, 46 and 48. This portion of the device's operation is illustrated in the flow chart in FIG. 9. In response to detection of a tachycardia which is determined to require treatment by a cardioversion pulse, microprocessor 2 may disable ventricular sensing by pacer circuitry 10 and at 812 causes control circuitry 4 to initiate charging of the output capacitors. During charging of the output capacitors, the microprocessor at 814 causes pacer/timing circuitry 10 to deliver an anti-tachycardia pacing therapy, as illustrated in FIG. 2. The pacing therapy delivered may simply be a pre-programmed therapy, for example adaptive burst pacing of a fixed number of pulses, as illustrated in FIG. 2, delivered during all high voltage charging. Alternatively, the number of pulses may be varied as a function of the voltage to which the capacitors are to be charged, so that more extended therapies may be available where allowed by longer charging times. As yet another alternative, especially in cases in which the delivery of a high voltage cardioversion pulse is scheduled due to detected acceleration of a tachycardia, the next scheduled pacing therapy which would have been delivered in the absence of acceleration may be delivered, with pulse number appropriately limited to ensure termination of anti-tachycardia pacing prior to the capacitors being fully charged.

Figure 10:
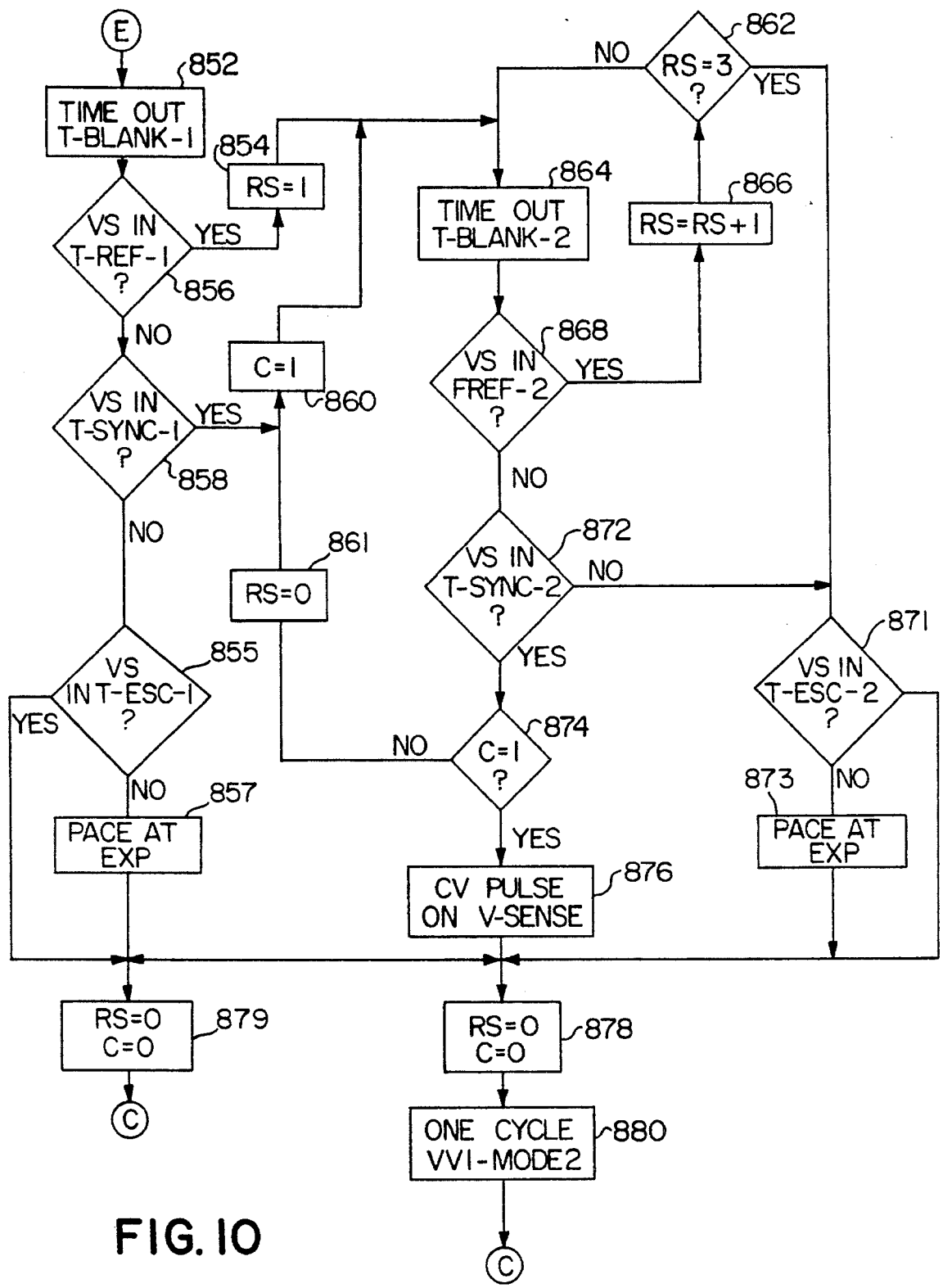

After completion of the anti-tachycardia pacing sequence, the device checks determine whether the high voltage capacitors are charged at 813. If so, confirmation and synchronization as illustrated in FIG. 10 is initiated. If the capacitors have not finished charging, the microprocessor 2 checks at 815 to determine whether the tachycardia has terminated. Termination may be detected as discussed above in conjunction with FIG. 8. If termination is detected, therapy is aborted and the high voltage capacitors are dumped at 810 (FIG. 8). If termination is not detected, the microprocessor checks at 816 to determine whether an excessive period of time has passed without the output capacitors reaching the charge level determined by microprocessor 2, as indicated by the signal on VCAP line 64. If not, the device continues to await capacitor charge-up and/or termination detection. If an excessive amount of time has passed, therapy is aborted at 818. For example, a period of 35 seconds without successful capacitor charging is appropriate in the context of the present invention. In the event that three consecutive attempts to charge the capacitors fail at 820, the microprocessor 2 disables additional charging cycles and VT/VF therapies and may trigger discharge of the output capacitors via a signal on DUMP line 62 from control circuit 4 if desired.

Figure 11:
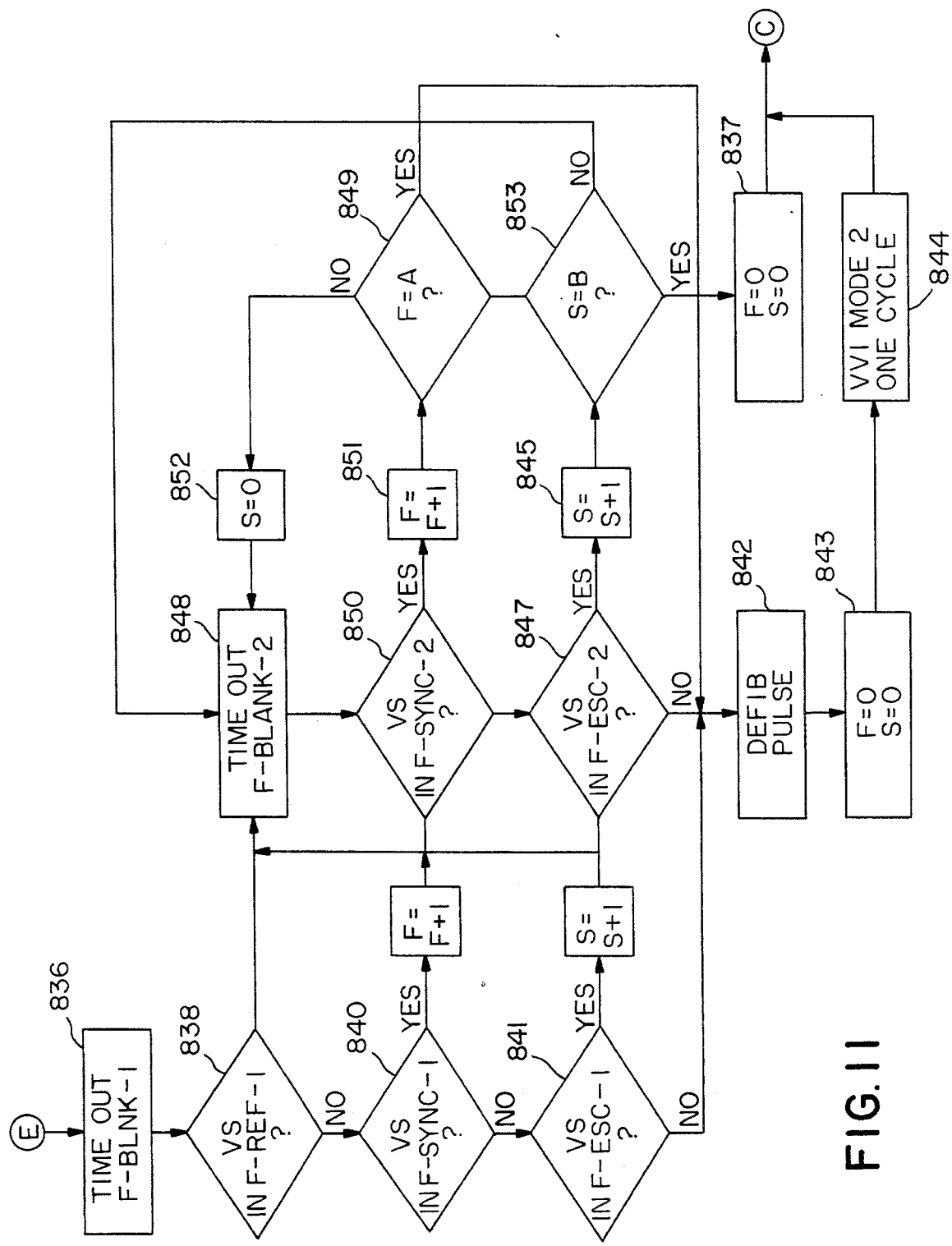

Similarly, after detection of ventricular fibrillation, ventricular sensing may be disabled and at 826 capacitor charging is initiated and anti-tachycardia pacing is delivered at 828. After completion of the anti-tachycardia pacing sequence, the device checks determine whether the high voltage capacitors are charged at 827. If so, confirmation and synchronization as illustrated in FIG. 11 is initiated. If the capacitors have not finished charging, the microprocessor 2 checks at 829 to determine whether the tachycardia has terminated. Termination may be detected as discussed above in conjunction with FIG. 8. If termination is detected, therapy is aborted and the high voltage capacitors are dumped at 810 (FIG. 8). If termination is not detected, the microprocessor checks at 830 to determine whether an excessive period of time has passed without the output capacitors reaching the charge level determined by microprocessor 2, as indicated by the signal on VCAP line 64. If not, the device continues to await capacitor charge-up and/or termination detection. If an excessive amount of time has passed, therapy is aborted at 818, as discussed above.

FIG. 10 illustrates the functional operation of the tachycardia confirmation and pulse synchronization functions following termination of high voltage charging. This portion of the operation of the device corresponds generally to the cardioversion pulse synchronization function as disclosed in U.S. Pat. No. 5,188,105, issued to Keimel, incorporated herein by reference in its entirety, with some modifications. In performing the confirmation and synchronization function, the microprocessor 2 employs the timers within pacer circuitry 10 to define time intervals associated with synchronization and confirmation cycles. Following detection of ventricular tachycardia and successful charging of the output capacitors, microprocessor 2 sets the timers in pacer circuitry 10 to define a first escape interval T-ESC-1, a first synchronization interval T-SYNC-1, a first refractory interval T-REF-1 and a first blanking interval T-BLANK-1. During T-BLANK-1 at 852, ventricular sensing is disabled. In response to an interrupt indicating ventricular sensing during T-REF-1 at 856, the microprocessor 2 notes the occurrence of the refractory sense at 854, and initiates timing of a second synchronization cycle including a second escape interval T-ESC-2 a second synchronization interval T-SYNC-2, a second refractory interval T-REF-2 and a second blanking interval T-BLANK-2.

In the event that no interrupt indicating the occurrence of ventricular sensing occurs during T-REF-1, the microprocessor continues to wait for the occurrence of an interrupt indicating ventricular sensing during T-SYNC-1. If an interrupt occurs, the microprocessor 2 notes it at 860, and initiates a second synchronization cycle, as discussed above. In the absence of sensed events occurring during T-SYNC-1, a return to sinus rhythm is presumed to have occurred. If a sensed event occurs during T-ESC-1, as detected at 855, the microprocessor 2 resets the internal flags at 879, and initiates VVI bradycardia pacing in Mode 1, as in FIG. 8. If no sensed event occurs during T-ESC-1, a pacing pulse is delivered at 857, at the expiration of T-ESC-1, prior to returning to VVI pacing.

In the event that a second synchronization cycle is initiated, the microprocessor 2 waits for an interrupt during T-REF-2 indicative of ventricular sensing. If such an interrupt occurs at 868, the microprocessor increments the count (RS) of sensed events occurring during refractory periods at 866, and checks to see whether three successive refractory sense events have occurred at 862. In response to refractory sense events occurring during the refractory intervals of three successive synchronization cycles, the microprocessor awaits the expiration of T-ESC-2. If a sensed event occurs during T-ESC-2 as detected at 871 the microprocessor 2 resets the internal flags at 879, and initiates VVI bradycardia pacing in Mode 1 , as in FIG. 8. If no sensed event occurs during T-ESC-2, a pacing pulse is delivered at 853, at the expiration of T-ESC-2, prior to returning to VVI pacing.

In the event that no R-waves are sensed during T-REF-2, the microprocessor 2 continues to wait for an interrupt indicating the occurrence of an R-wave during the post-refractory portion of T-SYNC-2, at 872. In the event that no such R-wave is sensed, a return to sinus rhythm is presumed. The microprocessor awaits the expiration of T-ESC-2. If a sensed event occurs during T-ESC-2, as detected at 871, the microprocessor 2 resets the internal flags at 879, and initiates VVI bradycardia pacing in Mode 1, as in FIG. 8. If no sensed event occurs during T-ESC-2, a pacing pulse is delivered at 873, at the expiration of T-ESC-2, prior to returning to VVI pacing.

In the event that the microprocessor 2 receives an interrupt indicating the occurrence of an R-wave during T-SYNC-2 at 872, the microprocessor checks at 874 to determine whether a previous R-wave has been sensed in the post-refractory portion of a synchronization interval. If an R-wave previously has been sensed in the post-refractory portion of a synchronization interval, the microprocessor 2 initiates delivery of a cardioversion pulse synchronized to the most recent R-wave interrupt at 876. Microprocessor 2 then resets all internal flags at 878, triggers one cycle of VVI bradycardia pacing in Mode 2 at 880. Mode 2 VVI pacing may, for example, employ an escape interval, a refractory interval and escape interval each 200 ms greater than the programmed parameters for VVI pacing, all initiated on delivery of the cardioversion pulse. The device then returns to bradycardia pacing in Mode 1 as in FIG. 8.

In the event that an R-wave is sensed during the post-refractory portion of T-SYNC-2 at 872, but there is no internal flag set indicating the occurrence of a previous post-refractory sensed R-wave at 874, the microprocessor sets RS=0 at 861, sets C=1 at 860 and initiates timing of the third synchronization cycle, employing the same time parameters as the second synchronization cycle.

The microprocessor 2 continues to define synchronization cycles having the time parameters of the second synchronization cycle until one of the synchronization intervals expires without ventricular sensing, R-waves occur within refractory intervals within three successive synchronization intervals, or two R-waves are sensed during the non-refractory portions of synchronization intervals. A maximum of five synchronization cycles are theoretically possible, but generally only two or three synchronization cycles are required.

FIG. 11 illustrates the functional operation of the fibrillation confirmation and synchronization function. In the confirmation and synchronization function for fibrillation, the microprocessor again employs the timers located within pacer circuitry 10 to define synchronization, refractory and blanking intervals associated with synchronization cycles. The timers within pacer circuitry 10 are initially set to define a first escape interval F-ESC-1, a first synchronization interval F-SYNC-1, a first refractory interval F-REF-1, and a first blanking interval F-BLANK-1, in order of descending duration.

During time out of F-BLANK-1at 836, ventricular sensing is disabled. After time out of F-BLANK-1, ventricular sensing is re-enabled by microprocessor 2, which waits for an interrupt indicating the occurrence of ventricular sensing during F-REF-1 at 838. If no interrupt is provided, the microprocessor continues to wait at 840 for an interrupt during the post-refractory portion of F-SYNC-1.

If no R-wave interrupt is received, microprocessor 2 the microprocessor continues to wait at 841 for/an interrupt during the post-refractory portion of F-ESC-1. If no R-wave interrupt is received, microprocessor 2 triggers control circuitry 4 to provide a defibrillation pulse at the end of F-ESC-1, at 842. After delivery of the defibrillation pulse, microprocessor 2 resets internal flags at 843 and at 844, sets the timers in pacer circuitry 10 to define a single cycle of VVI bradycardia pacing in Mode 2. After one cycle of VVI pacing in Mode 2, the microprocessor initiates bradycardia pacing in Mode 1 at the programmed parameters, as in FIG. 8. It should be noted that any residual voltage remaining on the output capacitors at this point is not discharged until detection of fibrillation termination at 806 or tachycardia termination at 808 (FIG. 8).

In the event that an R-wave interrupt occurs during the post-refractory portion of F-SYNC-1, as indicated at 840, microprocessor 2 identifies the sensed R-wave as indicative of fibrillation, increments the value of "F" by one and begins a second synchronization cycle. In the event that an R-wave interrupt occurs during the post-refractory portion of F-ESC-1, as indicated at 841, microprocessor 2 identifies the R-wave as indicative of a sinus rhythm, increments the value of "S" by one and begins a second synchronization cycle. In the event that an R-wave is sensed during F-REF-1, a second synchronization cycle is similarly begun.

In conjunction with the second synchronization cycle, microprocessor 2 employs the timers in pacer circuitry 10 to define a second escape interval F-ESC-2, a synchronization interval F-SYNC-2 and a second blanking interval F-BLANK-2, in order of descending duration. Timing of intervals associated with the first synchronization cycle terminates. During F-BLANK-2 at 848, ventricular sensing is disabled. Following time out of F-BLANK-2, the microprocessor 2 awaits for the occurrence of an R-wave-interrupt. If an R-wave interrupt occurs prior to expiration of F-SYNC-2, at 850, the microprocessor increments the value of "F" at 851 checks at 849 to determine whether a predetermined number "A" (typically 2) R-waves have been sensed during synchronization intervals. If so, a defibrillation pulse is triggered synchronized to the R-wave interrupt at 842. If not, the value of "S" is set to zero at 852, to reset the count of successive sinus R-waves and a third synchronization cycle is initiated, having the same parameters as the second cycle.

If no R-wave interrupt occurs prior to the expiration of F-SYNC-2, the microprocessor waits for the expiration of F-ESC-2 at 847. If an R-wave is sensed prior to time out of F-ESC-2, the value of "S" is incremented at 845 and the microprocessor checks at 853 to determine whether R-waves have occurred following the expiration of a predetermined number "B" (e.g. 2 or 3) of successive synchronization intervals. If so, a return to sinus rhythm is presumed, the microprocessor resets internal flags at 837 and the device returns to VVI pacing in Mode 1. If no R-wave occurs prior to time out of F-ESC-2, a defibrillation pulse is triggered at the expiration of F-ESC-2 at 842.

The synchronization and confirmation process continues until an escape interval passes with no sensed R-waves, R-waves occur within a total of "A" synchronization intervals or "B" successive R-waves occur following synchronization intervals. The output capacitors are not internally discharged until detection of NC termination, as discussed above.

Figure 3:
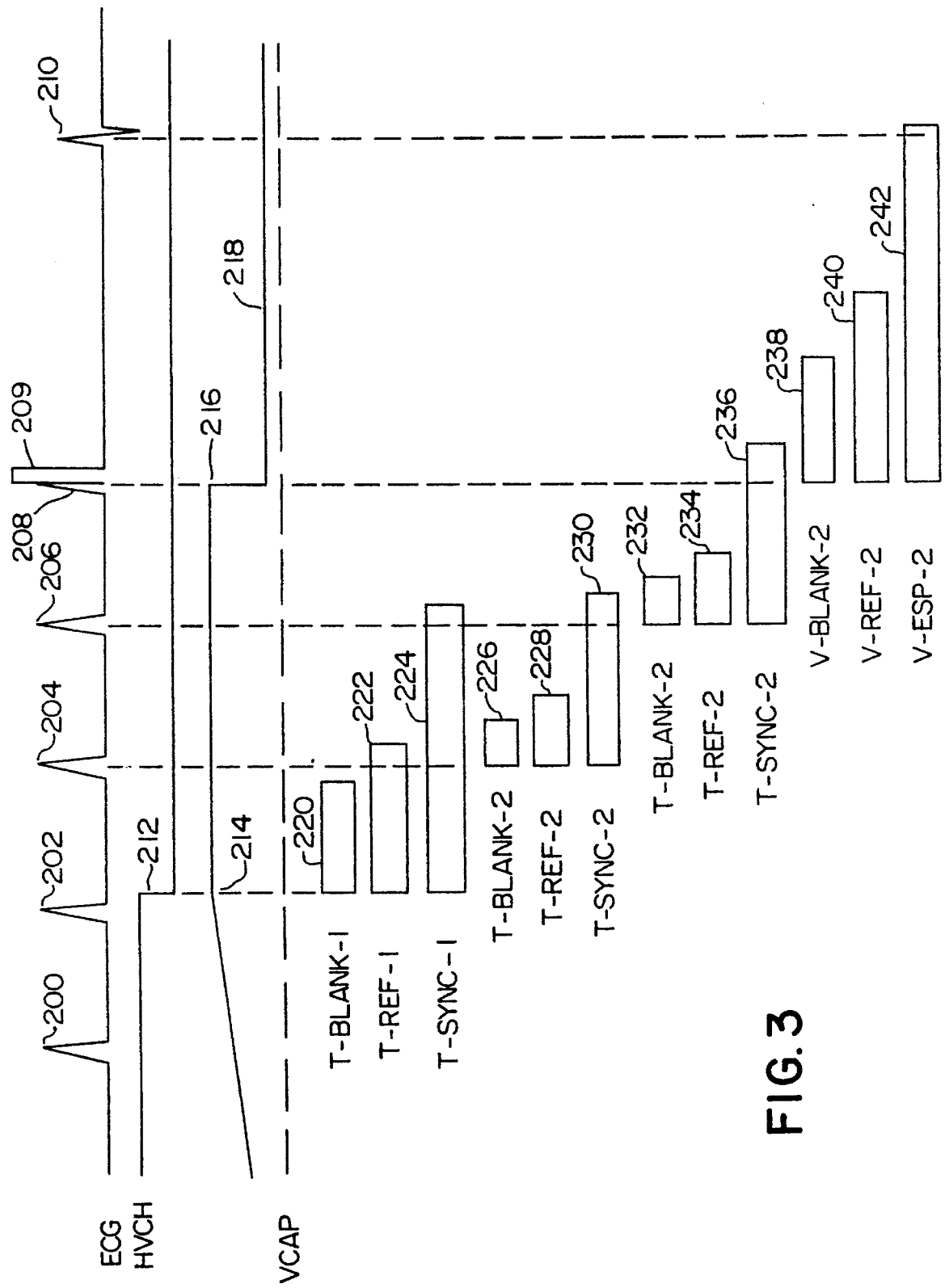
FIGS. 3 and 4 are timing diagrams illustrating the operation of a device embodying the present invention, following termination of anti-tachycardia pacing, as illustrated in FIG. 2, in the case where detection of ventricular tachycardia triggered charging of the high voltage output capacitors.
Figure 4:
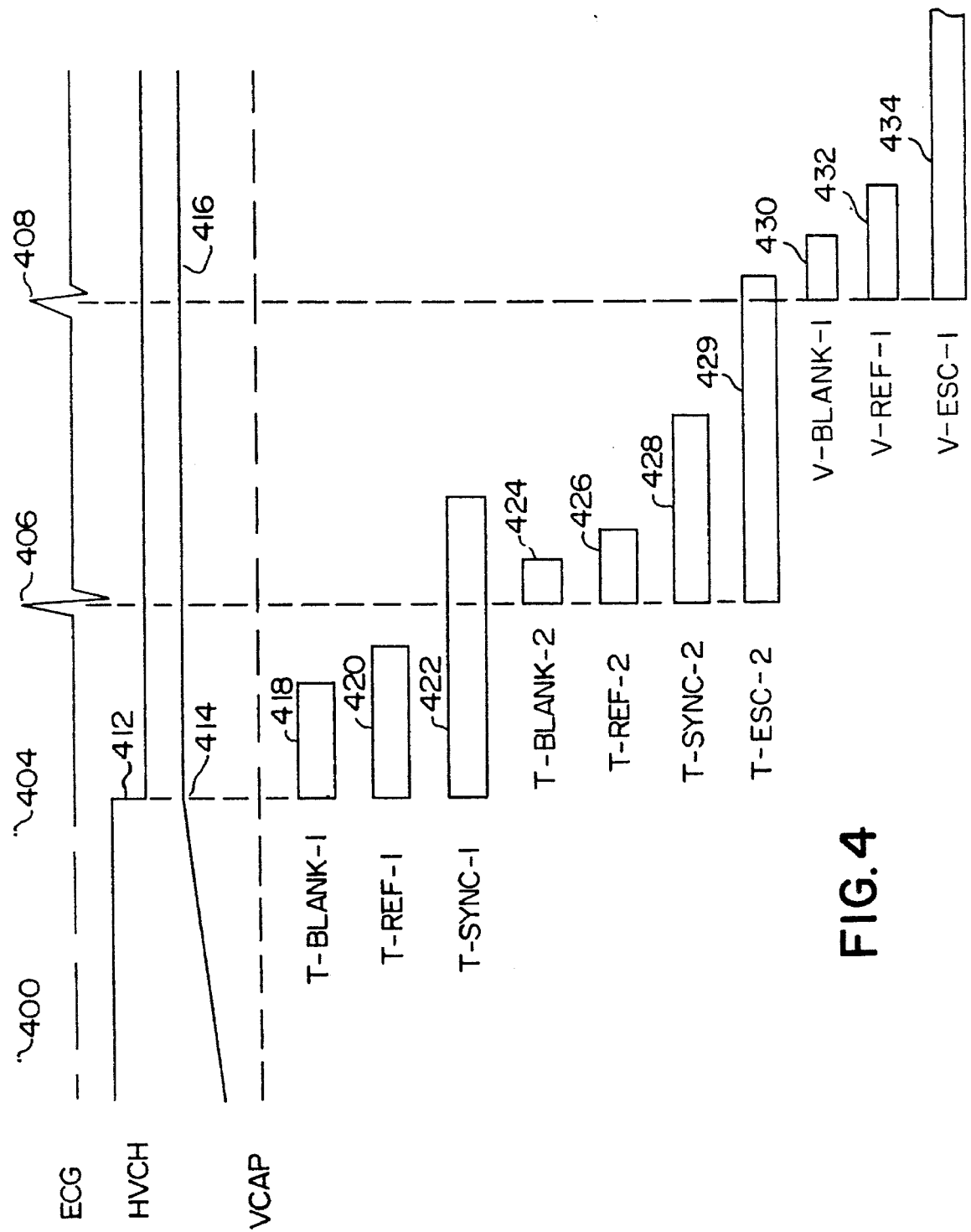
Figure 5:
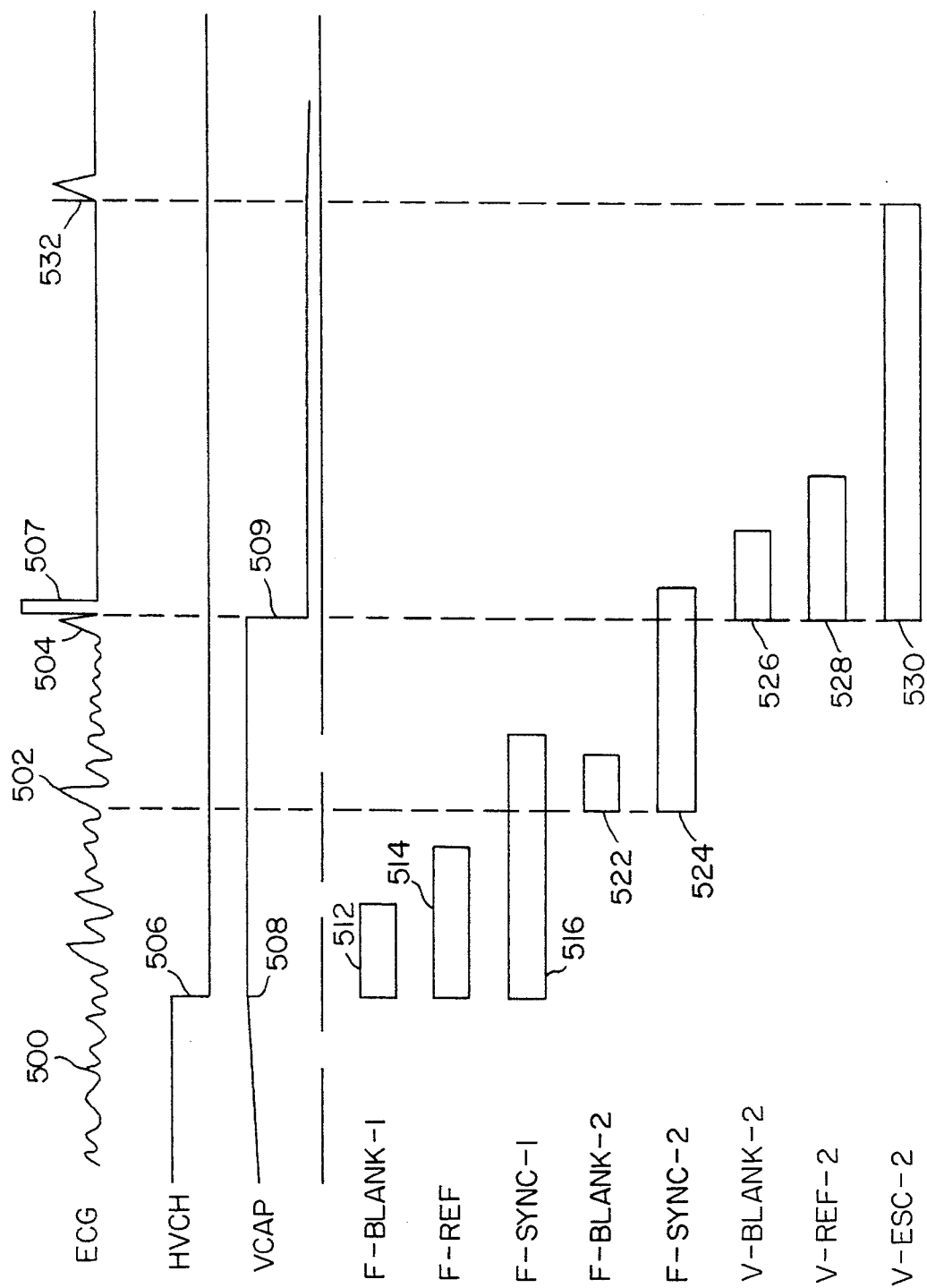
FIGS. 5, 6 and 7 are timing diagrams illustrating the operation of a device embodying the present invention, following termination of anti-tachycardia pacing, as illustrated in FIG. 2 in the case where detection of ventricular fibrillation triggered charging of the high voltage output capacitors.
Figure 6:
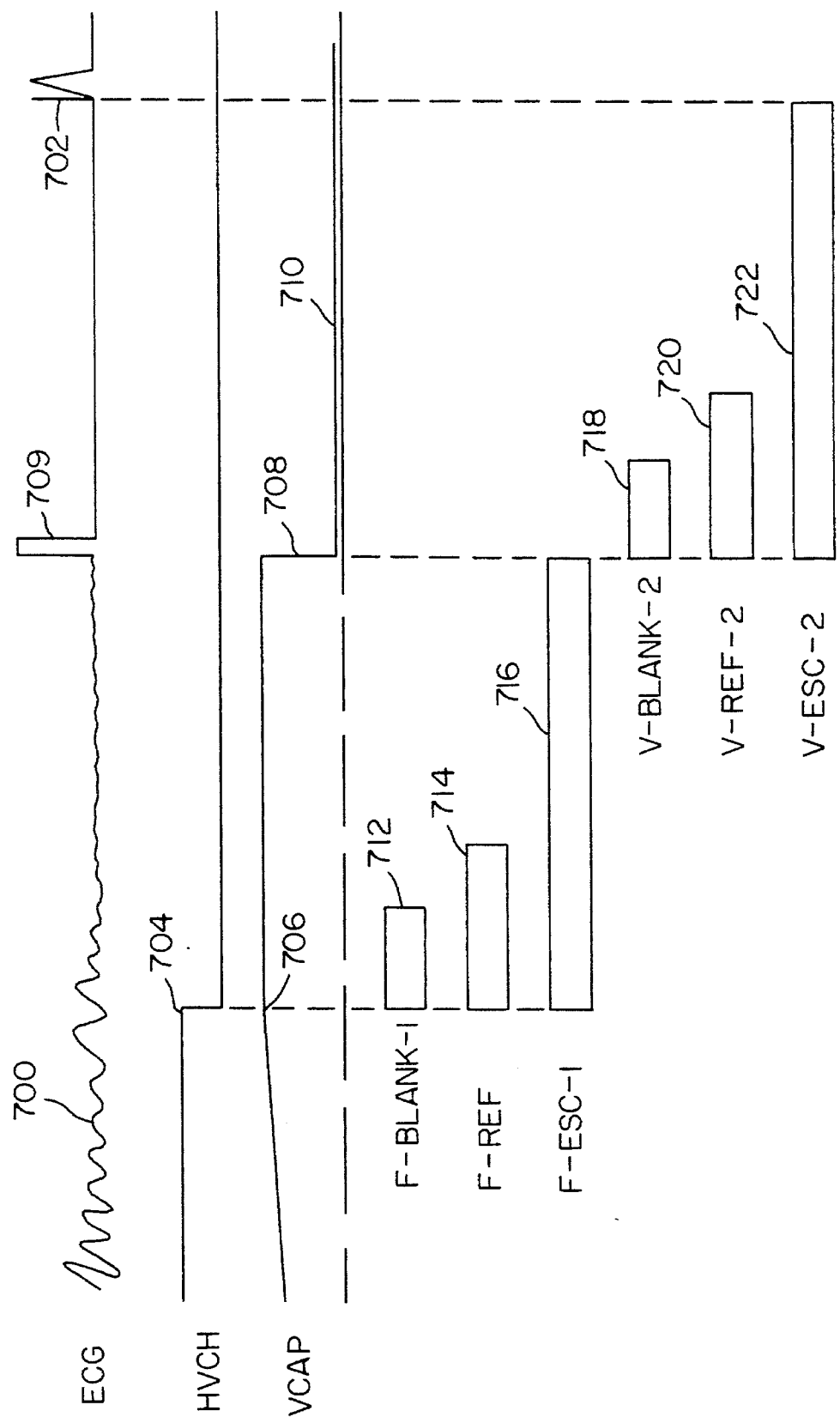
Figure 7:
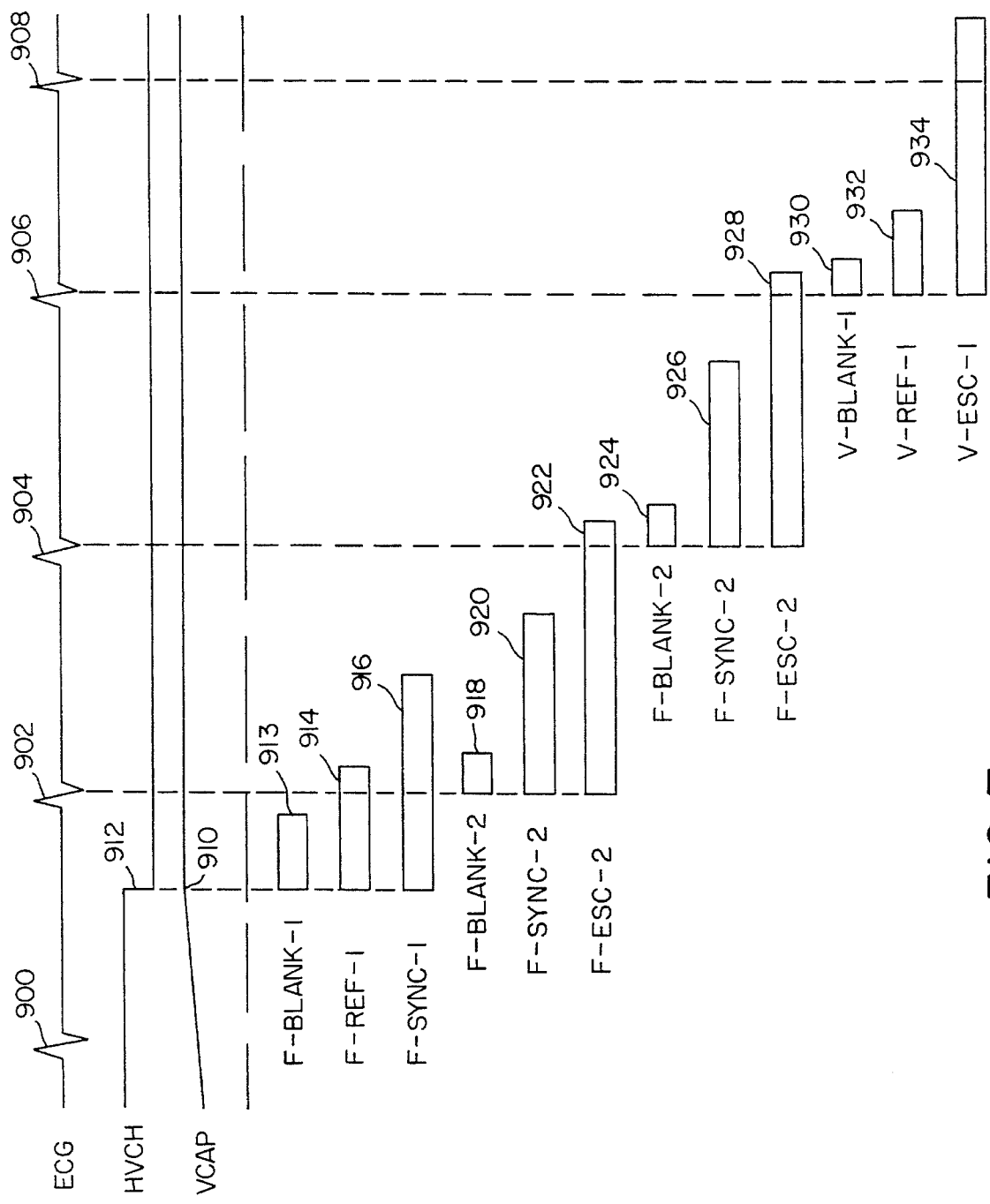

Exemplary simulated ECG's and associated timing diagrams for the confirmation and synchronization functions are set forth in FIGS. 3 through 7. FIGS. 3 and 4 illustrate the method of confirmation and synchronization employed following detection of tachycardia, delivery of anti-tachycardia pacing during charging and successful output capacitor charging. FIGS. 5 through 7 illustrate the method of confirmation and synchronization employed after detection of fibrillation and successful output capacitor charging.

FIG. 3 shows an simulated ECG strip, evidencing a ventricular tachycardia indicated by closely spaced R-waves 200, 202, 204, 206, 208 and 210. It is assumed that microprocessor 2 has already detected the occurrence of this tachyarrhythmia, and has enabled control circuitry 4 to initiate charging of the output capacitors by means of a high logic signal on HVCH line 54, and has triggered delivery of anti-tachycardia pacing. At point 214, the voltage on VCAP line 64 reaches the programmed voltage, and HVCH line 54 goes low at 214, terminating the charging process. Following the charging process, an initial blanking interval T-BLANK-1, 220, is defined. An appropriate duration for this blanking interval can be 300 ms. An initial refractory interval T-REF-1, 222, is also defined. An appropriate duration for this interval may be 400 ms.

An initial synchronization interval T-SYNC-1, 224, is also defined. The duration of this interval is preferably a function of the rate criterion for tachycardia detection. In particular, it is recommended that this interval be equal to the tachycardia detection interval (the R-R interval corresponding to the lower limit of the tachycardia rate detection criterion) plus a predetermined time increment associated with the blanking interval and ringing behavior of the sense amplifier, for example 360 ms. The duration of T-ESC-1, not illustrated, may be the programmed rate plus an increment, e.g. 300 ms.

R-wave 204 occurs during the refractory portion of the first synchronization interval 224, and initiates the second synchronization interval 230. A second blanking interval T-BLANK-2, 226, is also initiated. This interval may be, for example, 120 ms., and may correspond to the blanking interval used following ventricular sensing during bradycardia pacing or may be a separately defined value. Also initiated is a second refractory interval T-REF-2, 228, which may be, for example, 200 ms., and again may correspond either to the normal refractory interval employed by the device following sensed ventricular contractions, or may be separately defined.

The second synchronization interval T-SYNC-2, 224, is preferably also a function of the rate criterion as discussed above, and may be, for example, the tachycardia detection interval plus 60 ms. T-ESC-2, not illustrated, may be equal to the programmed escape interval for VVI pacing. R-wave 206 falls in the post-refractory portion of T-SYNC-2 interval 230, initiating a new synchronization cycle comprising T-BLANK-2 interval 232, T-REF-2 interval 234, T-SYNC-2 interval 236 and a T-ESC-2 interval, not illustrated. These intervals may correspond in duration to intervals 226, 228 and 230 in the previous synchronization cycle.

Because R-wave 208 is the second successive R-wave sensed within the post-refractory portion of a synchronization interval, it triggers delivery of a cardioversion pulse 209 due to discharge of the high voltage capacitors at 216, and initiates one cycle of mode 2 VVI bradycardia pacing. Following generation of the cardioversion pulse at 216, microprocessor 2 initiates a ventricular blanking interval V-BLANK-2, 238, a ventricular refractory interval V-REF-2, 240, and a ventricular escape interval V-ESC-2, 242, all of which may be equal to the programmed values for VVI pacing, plus an increment of 200 ms, as discussed above. Following sensing of R-wave 210, the device returns to VVI bradycardia pacing at programmed parameters (Mode 1).

The time periods indicated in the timing chart in FIG. 4 correspond to the time intervals discussed in conjunction with FIG. 3, and can be assumed to have identical durations. FIG. 4 illustrates the operation of the synchronization method in conjunction with a return to normal sinus rhythm, due to delivery of anti-tachycardia pacing as in FIG. 2. The simulated EKG strip shows a series of tachycardia beats 400, 404, 406, 408 indicative of sinus rhythm. Again, it is assumed that tachycardia has previously been detected that charging of the output capacitors has already been initiated and that the anti-tachycardia pacing therapy has already been delivered. On the capacitor reaching its programmed output voltage at 414, HVCH line 54 goes low, and the first synchronization interval 422 is initiated, along with the first refractory interval 420 and first blanking interval 418. R-wave 406 occurs during the post-refractory portion of synchronization interval 422, and initiates timing of the second synchronization interval 428 and associated refractory interval 426, escape interval 429 and blanking interval 424.

Because no R-waves are sensed during synchronization interval 428, the microprocessor cancels the scheduled cardioversion therapy, and returns the operation of the pacemaker/cardioverter/defibrillator to VVI bradycardia pacing in Mode 1, initiating a ventricular blanking period 430, ventricular refractory period 432 and ventricular escape interval 434. It should be noted that the output capacitors are not discharged in response to cancellation of the cardioversion therapy, but are instead maintained in their charged condition, as indicated at 416, until subsequent detection of tachycardia termination.

FIG. 5 illustrates the operation of the confirmation and synchronization method following detection of fibrillation. The simulated EKG illustrates ventricular fibrillation at 500. At 508, the output capacitors are successfully charged as indicated by return of HVCH line 54 to a low logic level at 506, and the first synchronization interval 516 is initiated. For purposes of synchronization following fibrillation detection, the first synchronization interval F-SYNC-1 may be a pre-set duration, for example 800 ms., or may be a function of the tachycardia detection interval. For example, at the duration of F-SYNC-1 may be set equal to the tachycardia detection interval plus 360 ms. The initial blanking interval F-BLANK-1, 512, may be set at 300 ms. and the initial refractory interval F-REF-1, 514, may be set at 400 ms. The escape interval F-ESC-1, not illustrated, may be set to the programmed rate plus 300 ms.

An R-wave is sensed at 502, during refractory period 514, initiating timing of the second synchronization interval F-SYNC-2, 524, and a second blanking interval F-BLANK-2, 522. The duration of F-SYNC-2 may correspond to the duration of the second synchronization interval T-SYNC-2, discussed above, based on the selected tachycardia detection interval plus an increment, e.g. 60 ms or may be a fixed interval. The duration of F-BLANK-2 can correspond to the normal blanking period following sensed ventricular contractions used during VVI pacing (e.g. 120 ms.), or may be a predetermined different fixed value. the escape interval F-ESC-2, not illustrated, may correspond to the programmed VVI escape interval.

A second R-wave is detected at 504, which occurs during the post-blanking portion of the second synchronization interval F-SYNC-2, 524, triggering delivery of a defibrillation pulse 507 by discharge of the high voltage capacitors at 509. Following delivery of the defibrillation pulse, the microprocessor 2 initiates a single cycle of VVI pacing in Mode 2, initiating an escape interval 530, a refractory interval 528 and a blanking interval 526 each corresponding to programmed values for VVI pacing plus 200 ms increments. At the expiration of escape interval 530, a ventricular pacing pulse 532 is delivered and the device returns to VVI pacing in Mode 1. It should be noted that the residual voltage 534 remaining on the output capacitors remains until detection of fibrillation termination.

FIG. 6 illustrates the operation of the defibrillation confirmation and synchronization function when it is impossible to deliver a synchronized defibrillation pulse. The simulated ECG illustrates a pattern 700 indicative of ventricular fibrillation. Upon successful charging of the output capacitors at 706, as indicated by the logic level on HVCH line 54 going low at 704, the first synchronization interval (not illustrated) is initiated, along with corresponding blanking, refractory and escape intervals 712, 714 and 716, respectively. Because no R-wave is sensed during escape interval 716, a defibrillation pulse 709 is triggered at the expiration of escape interval 716, by discharge of the high voltage capacitors at 708. The microprocessor 2 then returns the device to VVI bradycardia pacing for one cycle in mode 2, with corresponding defined escape interval 722, refractory period 720 and blanking interval 718, corresponding to the intervals discussed previously in conjunction with ventricular pacing in Mode 2. At expiration of escape interval 722, a ventricular pacing pulse 702 is generated, and the device thereafter performs VVI bradycardia pacing at the programmed parameters, pending redetection of fibrillation or tachycardia detection. The residual voltage 710 remaining on the output capacitors remains until detection of fibrillation termination.

FIG. 7 illustrates the situation in which the anti-tachycardia pacing during charging was effective in terminating the detected arrhythmia. This may happen, for example, in the situation in which the detected arrhythmia is, for example, a high rate ventricular tachycardia, ventricular flutter or ventricular flitter, which has been diagnosed by the device as ventricular fibrillation due to its short cycle length. Spontaneous R waves 900, 902, 904, 906 and 908 illustrate normal sinus rhythm. At 910, the capacitor is fully charged, and HVCH line 54 (FIG. 1) goes low at 912. The first synchronization cycle is initiated, along with corresponding blanking, refractory and synchronization intervals 913, 914 and 916, respectively. R wave 902 falls into the refractory period 914, and thus initiates a second synchronization cycle, with associated blanking, synchronization and escape intervals 918, 920 and 922, respectively. R wave 904 occurs outside the synchronization interval 920, but prior to expiration of the escape interval 922 and is thus assumed to be a normal sinus beat. A third synchronization cycle is initiated, along with associated blanking, refractory and escape intervals 924, 926 and 928, respectively. R wave 906 falls between the expiration of synchronization interval 926 and escape interval 928 and is thus also considered to be indicative of sinus rhythm. In the illustrated timing chart, it is assumed that the value of "B" (see FIG. 11) is set at 2, so two successive R waves 904 and 906 are sufficient to abort delivery of therapy. The device returns to bradycardia pacing in Mode 1 using the programmed parameters, initiating blanking, refractory and escape intervals 930, 983 and 934, as illustrated. The voltage on the output capacitors persists until detection of termination of fibrillation, as discussed above.

The above specification discloses a ventricular cardioverter/defibrillator. However, the invention described is also believed valuable in the context of an atrial cardioverter or defibrillator. Similarly, the described device allocates functional elements to particular portions and types of circuitry, employing a conventional division between a microprocessor and external timing and control circuitry. However, the device is also readily practiced in conjunction with other microprocessor based implementations, and may also be practiced in implementations employing full custom digital circuitry or analog circuitry to perform control and timing functions. As such, the above disclosure should be considered exemplary, rather than limiting with regard to the claims that follow.

In conjunction with the above disclosure, I claim:

1. An apparatus for treating tachyarrhythmias, comprising;

means for generating anti-tachycardia pacing pulse trains;

means for generating high energy pulses for delivery to a heart, comprising an output capacitor, means for charging said output capacitor and means for discharging said output capacitor through heart tissue;

means for detecting the occurrence of a tachyarrhythmia;

means for initiating charging of said output capacitor;

means for triggering delivery of a said anti-tachycardia pulse train, during the charging of said output capacitor;

means for determining whether said anti-tachycardia pulse train has terminated said tachyarrhythmia and for triggering discharge of said output capacitor through said heart tissue in response to the failure of said pulse train to terminate said tachyarrhythmia, wherein said detecting means comprises means for detecting fibrillation and wherein said determining means comprises means for detecting depolarizations of said heart following completions of charging of said output capacitor and means responsive to completions of charging of said output capacitor for defining first predetermined time intervals thereafter and wherein said determining means further comprises means for triggering discharge of said capacitor responsive to a failure to sense depolarizations of said heart within said first predetermined time intervals.

2. Apparatus according to claim 1, wherein said determining means further comprises means responsive to completions of charging of said output capacitor for defining second predetermined time intervals thereafter, shorter than said first predetermined intervals and expiring prior to expiration of said first predetermined time intervals and means for triggering discharge of said capacitor responsive to sensing depolarizations of said heart occurring within said predetermined second time intervals.

3. Apparatus according to claim 2, wherein said determining means further comprises means responsive to completions of charging of said output capacitor for defining third predetermined time intervals thereafter, extending from the expirations of said second time intervals until expirations of said first time intervals and means for preventing discharge of said capacitor through said heart responsive to sensing depolarizations of said heart occurring within said third predetermined time intervals.

4. An apparatus for treating tachyarrhythmias, comprising:

means for generating anti-tachycardia pacing pulse trains;

means for generating high energy pulses for delivery to a heart, comprising an output capacitor, means for charging said output capacitor and means for discharging said output capacitor through heart tissue;

means for detecting the occurrence of a tachyarrhythmia;

means for initiating charging of said output capacitor;

means for triggering delivery of a said anti-tachycardia pulse train, during the charging of said output capacitor;

means for determining whether said anti-tachycardia pulse train has terminated said tachyarrhythmia and for triggering discharge of said output capacitor through said heart tissue in response to the failure of said pulse train to terminate said tachyarrhythmia, wherein said detecting means comprises means for detecting tachycardia and wherein said determining means comprises means detecting depolarizations of said heart following charging of said output capacitor and means responsive to completions of charging of said output capacitor for defining first predetermined time intervals thereafter and wherein said determining means comprises means for preventing discharge of said capacitor responsive to failures to sense depolarizations of said heart within said first predetermined time intervals.

5. Apparatus according to claim 4, wherein said determining means further comprises means responsive to completions of charging of said output capacitor for defining second predetermined time intervals thereafter, shorter than said first predetermined intervals expiring before expiration of said first predetermined time intervals and means for triggering discharge of said capacitor through said heart responsive to sensing depolarizations of said heart occurring within said predetermined second time intervals.

6. Apparatus according to claim 5, wherein said determining means further comprises means responsive to completions of charging of said output capacitor for defining third predetermined time intervals thereafter, extending from the expirations of said second time intervals until expirations of said first time intervals and means for preventing discharge of said capacitor through said heart responsive to sensing depolarizations of said heart occurring within said third predetermined time intervals.

7. An apparatus for treating a tachyarrhythmia of a chamber of a heart, comprising:

means for detecting a tachyarrhythmia in said chamber;

means for diagnosing a detected tachyarrhythmia as fibrillation of said chamber;

means for generating an anti-tachycardia pulse train;

means for generating high energy pulses for delivery to the heart, comprising an output capacitor, means for charging said output capacitor and means for discharging said output capacitor through heart tissue;

means responsive to diagnosing of fibrillation in said chamber for initiating charging of said output capacitor;

means responsive to diagnosing fibrillation in said chamber for triggering delivery of said anti-tachycardia pulse train, during the charging of said output capacitor;

means for determining whether said anti-tachycardia pulse train has terminated said detected tachyarrhythmia and for triggering discharge of said output capacitor through said heart in response to the failure of said pulse train to terminate said detected tachyarrhythmia.

8. An apparatus for treating a tachyarrhythmia of a chamber of a heart, comprising:

means for detecting a tachyarrhythmia in said chamber;

means for generating an anti-tachycardia pulse train;

means for generating high energy pulses for delivery to the heart, comprising an output capacitor, means for charging said output capacitor to a voltage appropriate for defibrillation and means for discharging said output capacitor through heart tissue;

means responsive to detection of a tachyarrhythmia in said chamber for triggering charging of said output capacitor to a voltage appropriate for defibrillation;

means responsive to detection of a tachyarrhythmia in said chamber for triggering delivery of said anti-tachycardia pulse train, during the charging of said output capacitor;

means for determining whether said anti-tachycardia pulse train has terminated said detected tachyarrhythmia and for triggering discharge of said output capacitor through said heart in response to the failure of said pulse train to terminate said detected tachyarrhythmia.

9. A method for treating a tachyarrhythmia of a chamber of a heart, comprising:
   detecting a tachyarrhythmia in said chamber;
   diagnosing a detected tachyarrhythmia as fibrillation of said chamber;
   responsive to diagnosing of fibrillation in said chamber, initiating charging of a capacitor;
   responsive to diagnosing fibrillation in said chamber, delivering an anti-tachycardia pulse train to said chamber, during the charging of said output capacitor;
   determining whether said anti-tachycardia pulse train has terminated said detected tachyarrhythmia; and;
   discharging said capacitor through said heart in response to the failure of said pulse train to terminate said detected tachyarrhythmia.

10. A method for treating a tachyarrhythmia of a chamber of a heart, comprising:
    detecting a tachyarrhythmia in said chamber;
    responsive to detecting a said tachyarrhythmia in said chamber, charging of a capacitor to a voltage appropriate for defibrillation;
    responsive to diagnosing fibrillation in said chamber, delivering an anti-tachycardia pulse train to said chamber, during the charging of said output capacitor;
    determining whether said anti-tachycardia pulse train has terminated said detected tachyarrhythmia; and
    discharging said capacitor through said heart to defibrillate said chamber in response to the failure of said pulse train to terminate said detected tachyarrhythmia.

11. A method of treating tachyarrhythmias is a patient's heart, comprising:
    detecting occurrences of a tachyarrhythmia;
    in response to detecting occurrences of said tachyarrhythmia, initiating charging of a high voltage capacitor;
    delivering anti-tachycardia pulse trains, during charging of said capacitor;
    determining whether said a said anti-tachycardia pulse trains have terminated said tachyarrhythmia and discharging said capacitor through said heart in response to failures of said pulse trains to terminate said tachyarrhythmia;
    wherein said detecting step comprises detecting occurrences of fibrillation and wherein said determining step comprises detecting depolarizations of said heart following completions of charging of said output capacitor, and responsive to completions of charging of said output capacitor, defining first predetermined time intervals thereafter and wherein said discharging step comprises discharging said capacitor responsive to failures to sense a depolarization of said heart within said first predetermined time intervals.

12. A method according to claim 11, wherein said determining step further comprises responsive to completions of charging of said output capacitor, defining second predetermined time intervals thereafter, shorter than said first predetermined intervals and expiring prior to expiration of said first predetermined time intervals and said discharging step comprises discharging said capacitor responsive to sensing depolarizations of said heart occurring within said predetermined second time intervals.

13. Apparatus according to claim 12, wherein said determining step further comprises, responsive to completions of charging of said output capacitor, defining third predetermined time intervals thereafter, extending from the expirations of said second time intervals until expirations of said first time intervals and said method further comprises preventing discharge of said capacitor through said heart responsive to sensing depolarizations of said heart occurring within said third predetermined time intervals.

14. A method of treating tachyarrhythmias in a patient's heart, comprising:
    detecting occurrences of a tachyarrhythmia;
    in response to occurrences of said tachyarrhythmia, initiating charging of a high voltage capacitor;
    delivering anti-tachycardia pulse trains, during the charging of said capacitor;
    determining whether said anti-tachycardia pulse trains have terminated said tachyarrhythmias and discharging said capacitor through said heart in response to failures of said pulse trains to terminate said tachyarrhythmia;
    wherein said detecting means comprises means for detecting tachycardia and wherein said determining step comprises detecting depolarizations of said heart following charging of said output capacitor and, responsive to completions of charging of said output capacitor defining first predetermined time intervals thereafter and said method further comprises preventing discharge of said capacitor responsive to failures to sense depolarizations of said heart within said first predetermined time intervals.

15. A method according to claim 14, wherein said determining step further comprises, responsive to completions of charging of said output capacitor, defining second predetermined time intervals thereafter, shorter than said first predetermined intervals and expiring prior to expiration of said first predetermined time intervals and said discharging step comprises discharging said capacitor through said heart responsive to sensing depolarizations of said heart occurring within said predetermined second time intervals.

16. A method according to claim 15, wherein said determining step further comprises, responsive to completions of charging of said output capacitor, defining third predetermined time intervals thereafter, extending from the expirations of said second time intervals until expirations of said first time intervals and said method further comprises preventing discharge of said capacitor through said heart responsive to sensing depolarizations of said heart occurring within said third predetermined time intervals.

17. An apparatus for treating a tachyarrhythmia of a chamber of a heart, comprising:
    means for detecting a tachyarrhythmia in said chamber;
    means for diagnosing a detected tachyarrhythmia as fibrillation of said chamber;
    means for generating pulse trains;
    means for generating high energy pulses for delivery to the heart, comprising an output capacitor, means for charging said output capacitor and means for discharging said output capacitor, after charging, through heart tissue;
    means responsive to diagnosing of fibrillation in said chamber for initiating charging of said output capacitor; and
    means responsive to diagnosing fibrillation in said chamber for triggering delivery of a said pulse train, during the charging of said output capacitor.

18. A method for treating a tachyarrhythmia of a chamber of a heart, comprising:

detecting a tachyarrhythmia in said chamber;

diagnosing a detected tachyarrhythmia as fibrillation of said chamber;

responsive to diagnosing of fibrillation in said chamber, initiating charging of a capacitor;

responsive to diagnosing fibrillation in said chamber, delivering a pulse train to said chamber, during the charging of said output capacitor, and;

discharging said capacitor through said heart following delivery of said pulse train.

* * * * *